(12) United States Patent
Yiu

(10) Patent No.: US 10,640,440 B2
(45) Date of Patent: May 5, 2020

(54) METHANOL PROCESS

(71) Applicant: JOHNSON MATTHEY DAVY TECHNOLOGIES LIMITED, London (GB)

(72) Inventor: Kar Chi Yiu, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 185 days.

(21) Appl. No.: 16/067,927

(22) PCT Filed: Dec. 16, 2016

(86) PCT No.: PCT/GB2016/053959
§ 371 (c)(1),
(2) Date: Jul. 3, 2018

(87) PCT Pub. No.: WO2017/121980
PCT Pub. Date: Jul. 20, 2017

(65) Prior Publication Data
US 2020/0087232 A1      Mar. 19, 2020

(30) Foreign Application Priority Data

Jan. 15, 2016   (GB) .................................. 1600793.2

(51) Int. Cl.
*C07C 29/15*      (2006.01)
*C07C 29/152*     (2006.01)
(Continued)

(52) U.S. Cl.
CPC ............. *C07C 29/152* (2013.01); *B01J 19/24* (2013.01); *C07C 29/15* (2013.01); *C07C 31/04* (2013.01); *C07C 29/1516* (2013.01)

(58) Field of Classification Search
None
See application file for complete search history.

(56) References Cited

U.S. PATENT DOCUMENTS 3,458,289 A    7/1969   King et al.
3,475,136 A    10/1969  Eschenbrenner et al.
(Continued)

FOREIGN PATENT DOCUMENTS

DE           3518362 A1      11/1986
WO   WO 2012/146904 A1      11/2012
(Continued)

OTHER PUBLICATIONS

PCT/GB2016/053959 International Search Report and Written Opinion dated Apr. 4, 2017.
(Continued)

*Primary Examiner* — Medhanit W Bahta
(74) *Attorney, Agent, or Firm* — BakerHostetler

(57) ABSTRACT

A process is described for the synthesis of methanol comprising the steps of: (i) passing a first synthesis gas mixture comprising a make-up gas and a first loop recycle gas stream through a first synthesis reactor containing a cooled methanol synthesis catalyst to form a first product gas stream, (ii) recovering methanol from the first product gas stream thereby forming a first methanol-depleted gas mixture, (iii) combining the first methanol-depleted gas mixture with a second loop recycle gas stream to form a second synthesis gas mixture, (iv) passing the second synthesis gas mixture through a second synthesis reactor containing a cooled methanol synthesis catalyst to form a second product gas stream, (v) recovering methanol from the second product gas stream thereby forming a second methanol-depleted gas mixture, and (vi) forming the first and second loop recycle gas streams from the second methanol-depleted gas mixture, wherein the first synthesis reactor has a higher heat transfer per cubic metre of catalyst than the second synthesis reactor and the recycle ratio of the first loop recycle gas stream to form the first synthesis gas mixture is in the range 0.1 to 1:1, (Continued)

and the recycle ratio of the second loop recycle gas stream to form the second synthesis gas mixture is in the range 1.1:1 to 6:1.

23 Claims, 2 Drawing Sheets

(51) Int. Cl.
*C07C 31/04* (2006.01)
*B01J 19/24* (2006.01)
*C07C 29/151* (2006.01)

(56) References Cited

U.S. PATENT DOCUMENTS

| | | | |
|---|---|---|---|
| 4,321,234 | A | 3/1982 | Ohsaki et al. |
| 4,411,877 | A | 10/1983 | Notman et al. |
| 5,631,302 | A | 5/1997 | Konig et al. |
| 5,827,901 | A | 10/1998 | Konig et al. |
| 7,790,775 | B2 | 9/2010 | Early |
| 8,536,235 | B2 | 9/2013 | Fitzpatrick |
| 8,629,191 | B2 | 1/2014 | Kopetsch et al. |
| 2011/0065966 | A1 | 3/2011 | Mueller et al. |
| 2014/0031438 | A1 | 1/2014 | Hackel et al. |
| 2016/0107961 | A1* | 4/2016 | Modarresi ............ B01J 8/0292 |

FOREIGN PATENT DOCUMENTS

| | | |
|---|---|---|
| WO | WO 2014/012601 A1 | 1/2014 |
| WO | WO 2014/206635 A1 | 12/2014 |

OTHER PUBLICATIONS

GB 1600793.2 Search Report under Section 17(5) dated Nov. 10, 2016.
GB 1621443.9 Combined Search and Examination Report under Sections 17 and 18(3) dated Sep. 25, 2017.
Johnson Matthey Davy Technologies, Oct. 2015, "Synthesis", davyprotech.com. Available from: https://web.archive/web20151023025714/http://davyprotech.com/what-we-do-licensed-processes-and-core-technologies/core-technologies/synthesis/specification/ [Archived entry date—Oct. 23, 2015].
Landalv, et al., Environmental Progress & Sustainable Energy, vol. 33, No. 3, pp. 744-750, first published May 19, 2014.
S.Nielsen et al., Topsoe Ammonia & Methanol Co-Production, Haldor Topsoe, pp. 1-18, Publication 2012.

* cited by examiner

METHANOL PROCESS

CROSS-REFERENCE TO RELATED APPLICATIONS

This application is the National Stage of International Patent Application No. PCT/GB2016/053959, filed Dec. 16, 2016, which claims priority from Great Britain Patent Application No. 1600793.2, filed Jan. 15, 2016, the disclosures of each of which are incorporated herein by reference in their entireties for any and all purposes.

This invention relates to a process for synthesising methanol.

Methanol synthesis is generally performed by passing a synthesis gas comprising hydrogen, carbon oxides and any inert gases at an elevated temperature and pressure through one or more beds of a methanol synthesis catalyst, which is often a copper-containing composition. Methanol is generally recovered by cooling the product gas stream to below the dew point of the methanol and separating off the product as a liquid. The crude methanol is typically purified by distillation. The process is often operated in a loop: thus the remaining unreacted gas stream is usually recycled to the synthesis reactor as part of the synthesis gas via a circulator. Fresh synthesis gas, termed make-up gas, is added to the recycled unreacted gas to form the synthesis gas stream. A purge stream is often taken from the circulating gas stream to avoid the build-up of inert gasses.

The process may be operated using two synthesis reactors each containing a bed of methanol synthesis catalyst.

U.S. Pat. No. 7,790,775 discloses a process for use in equilibrium exothermic gas phase reactions comprising the steps of (a) providing a recycle stream with the addition of make-up gas, to form a feed gas stream; (b) heating the feed gas stream; (c) passing the heated feed gas stream to a first reactor containing a catalyst for the exothermic gas phase reactions at conditions suitable for the reaction; (d) removing a product stream comprising product and unreacted gases from the first reactor; (e) cooling and partially condensing the product stream to form a gas phase and a liquid phase; (f) separating the liquid phase containing the desired product from the product stream and removing said liquid phase; (g) separating the gas phase from the product stream to form a gas stream; (h) optionally mixing the gas stream from the product stream with additional make-up gas; (i) heating the gas stream; (j) passing the heated gas stream to a final reactor containing a catalyst for the exothermic gas phase reactions at conditions suitable for the reaction; (k) removing a final product stream comprising product and unreacted gases from the final reactor; (l) cooling and partially condensing the final product stream to form a final gas phase and a final liquid phase; (m) separating the final liquid phase containing the desired product from the final product stream and removing said final liquid phase; and (n) separating the gas phase from the final product stream and recycling the gas to step (a); and in which the gas stream from step (g) is compressed prior to heating in step (i).

U.S. Pat. No. 8,536,235 discloses a process for the synthesis of methanol comprising the steps of: (a) passing a synthesis gas mixture comprising a loop gas and a make-up gas through a first synthesis reactor containing a methanol synthesis catalyst, said reactor cooled by boiling water under pressure, to form a mixed gas containing methanol, (b) cooling the mixed gas containing methanol, (c) passing said cooled mixed gas containing methanol through a second synthesis reactor containing a methanol synthesis catalyst in which further methanol is synthesised to form a product gas stream, (d) cooling said product gas to condense methanol, (e) recovering said methanol and returning unreacted gas as the loop gas to said first synthesis reactor, wherein the mixed gas containing methanol from the first synthesis reactor is cooled in heat exchange with either said loop gas or said make-up gas.

U.S. Pat. No. 5,827,901 describes a process in which methanol is produced from a synthesis gas containing hydrogen and carbon oxides on copper-containing catalysts at pressures in the range 20 to 120 bar and temperatures in the range 130 DEG to 350 DEG C. The synthesis gas is first of all passed through a first synthesis reactor, in which the catalyst is provided in tubes surrounded by water as a coolant, which is boiling at an elevated pressure. From the first reactor a first mixture containing gases and methanol vapour is withdrawn and passed without cooling through a second synthesis reactor. In the second reactor the catalyst is cooled with synthesis gas to which a make-up gas has been added.

U.S. Pat. No. 8,629,191 describes a process for producing methanol from a synthesis gas containing hydrogen and carbon oxides wherein the synthesis gas is passed through a first, water-cooled reactor in which a part of the carbon oxides is catalytically converted to methanol. The resulting mixture containing synthesis gas and methanol vapour is supplied to a second, gas-cooled reactor in which a further part of the carbon oxides is converted to methanol. Subsequently, methanol is separated from the synthesis gas, and synthesis gas is recirculated to the first reactor. The cooling gas flows through the second reactor co-current to the mixture withdrawn from the first reactor.

U.S. Pat. No. 5,631,302 describes a process in which methanol is catalytically produced from a synthesis gas containing hydrogen and carbon oxides on copper-containing catalysts under pressures in the range from 20 to 20 bars and at temperatures in the range from 200 to 350 DEG C. The synthesis gas is passed through a first synthesis reactor, which consists of a shaft reactor and contains a fixed bed of a copper-containing catalyst. The reaction in the shaft reactor is carried out adiabatically and without a recycling of synthesis gas. Together with recycle gas, the gas mixture which has not been reacted in the first synthesis reactor is passed through a second synthesis reactor, which contains a copper-containing catalyst, which is disposed in tubes and is indirectly cooled through boiling water.

US 2014/0031438 A1 describes a method for producing methanol from inert-rich syngas by installing a catalytic pre-reactor upstream of a single or multi-stage synthesis loop, a first part of the syngas being converted to methanol in the catalytic pre-reactor. In addition, an inert gas separation stage, for example a pressure swing adsorption system or a membrane system, is connected downstream of the synthesis loop, whereby a hydrogen-enriched syngas stream can be returned to the synthesis loop. In the processing of methane-rich syngas, the inert gas separation stage may also comprise an autothermal reformer in which methane is converted to carbon oxides and hydrogen, which are also returned into the synthesis loop.

WO 2014/012601 A1 describes a process for producing methanol comprising the steps of (a) providing a fresh methanol synthesis gas containing hydrogen, carbon monoxide and carbon dioxide; (b) providing a recycle gas stream containing unconverted methanol synthesis gas and mixing a part of the recycle stream with the fresh synthesis gas to form a process gas stream;

(c) introducing and reacting the process gas stream in a first methanol reaction unit in presence of a methanol catalyst and obtaining a first effluent stream containing methanol and a part of the unconverted synthesis gas contained in the recycle stream; and (d) introducing and reacting at least another part of the recycle gas stream in a second methanol reaction unit in presence of a methanol catalyst and obtaining a second effluent stream containing methanol and another part of the unconverted synthesis gas contained in the recycle stream, wherein the recycle stream is pressurised by a common circulator.

WO 02014/206635 A1 describes a process for the preparation of methanol in parallel reactors, comprising the steps of (a) reacting carbon oxides and hydrogen in the presence of a methanol catalyst in a first methanol reactor to obtain a first methanol-containing effluent, (b) introducing and reacting unconverted synthesis gas in a second methanol reactor in the presence of a methanol catalyst to obtain a second methanol-containing effluent, the first methanol reactor and the second methanol reactor being connected in parallel, (c) combining the first and second effluent, and (d) cooling and separating the combined and cooled effluent into a methanol-containing liquid phase and unconverted synthesis gas, wherein the methanol catalyst in the first methanol reactor is indirectly cooled by boiling water and the methanol catalyst in the second methanol reactor is either directly or indirectly cooled by the unconverted synthesis gas prior to conversion into the second effluent.

DE 3518362 A1 describes a process for producing methanol where, starting from a conventional methanol synthesis process in which unreacted synthesis gas is recycled to the inlet of the reactor, a methanol synthesis reactor which operates without recycling is arranged upstream of the recycling process.

We have realised that the efficiency of multiple-stage methanol synthesis may be improved by using different recycle ratios for different types of reaction reactor.

Accordingly the invention provides a process for the synthesis of methanol comprising the steps of:
(i) passing a first synthesis gas mixture comprising a make-up gas and a first loop recycle gas stream through a first synthesis reactor containing a cooled methanol synthesis catalyst to form a first product gas stream,
(ii) recovering methanol from the first product gas stream thereby forming a first methanol-depleted gas mixture,
(iii) combining the first methanol-depleted gas mixture with a second loop recycle gas stream to form a second synthesis gas mixture,
(iv) passing the second synthesis gas mixture through a second synthesis reactor containing a cooled methanol synthesis catalyst to form a second product gas stream,
(v) recovering methanol from the second product gas stream thereby forming a second methanol-depleted gas mixture, and
(vi) forming the first and second loop recycle gas streams from the second methanol-depleted gas mixture,
wherein the first synthesis reactor has a higher heat transfer per cubic metre of catalyst than the second synthesis reactor and the recycle ratio of the first loop recycle gas stream to form the first synthesis gas mixture is in the range 0.1 to 1:1, and the recycle ratio of the second loop recycle gas stream to form the second synthesis gas mixture is in the range 1.1:1 to 6:1.

Using different recycle ratio enables dilution of the loop gases to the preferred inlet compositions for the different reactors. The present invention reaps the benefit of using the different types of reactor because the synthesis gas is first reacted in a reactor that favours high reactant concentration, taking advantage of the high rate of reaction at high concentration.

The penalty of using such reactor is then removed by passing the synthesis gas to the second reactor that favours lower reaction rate, while reaping the benefit of higher feed efficiency. Importantly, the dilution stream for the first reactor has the least rate-determining reactant, which means the required recycle flow to achieve the required dilution is minimised.

The present invention utilises the advantages of each type of reaction reactor, hence it has a low recycle ratio section for the first synthesis reactor and a high recycle ratio section for the second synthesis reactor.

By the term "recycle ratio", we mean the molar flow ratio of the recycled loop gas to the make-up gas that form the synthesis gas mixtures fed to the first and second synthesis reactors. Accordingly the recycle ratio for the first synthesis gas arises from the proportion of the loop recycle gas combined with a make-up gas, and the recycle ratio for the second synthesis gas arises from the proportion of the loop gas combined with the first methanol-depleted gas mixture, both expressed relative to the make-up gas.

The recycle ratio to form the first synthesis gas mixture fed to the first synthesis reactor is in the range 0.1:1 to 1:1. Whereas the recycle ratio to form the second synthesis gas mixture fed to the second synthesis reactor may be 1.1:1 to 6:1, it is preferably in the range 1.5:1 to 6:1, more preferably 2:1 to 6:1.

The prior art processes having recycle of a loop gas to multiple reactors either do not have the ability to operate multiple reactors with different recycle ratios or do not disclose operating with different recycle ratios.

The first synthesis gas comprises a make-up gas. Make-up gas typically comprises hydrogen, carbon monoxide, and/or carbon dioxide. The make-up gas may be generated by the steam reforming of methane or naphtha using established steam reforming processes, including pre-reforming. However the present invention is of particular effectiveness in utilising reactive synthesis gases generated by processes including a step of partial oxidation of a hydrocarbon, biomass or carbonaceous feedstock. By "reactive synthesis gases" we mean a synthesis gas comprising hydrogen, carbon monoxide and carbon dioxide in which the ratio (by volume) of hydrogen to the total carbon oxides is ≥2:1. Such processes include combined reforming in which a first portion of a hydrocarbon feedstock is subjected to steam reforming and a second portion is subjected to autothermal reforming; and from coal or biomass gasification. Alternatively, off-gases from refineries or other chemical processes comprising principally hydrogen and carbon oxides (mainly as carbon monoxide) may also be used. In the present invention, the make-up gas preferably contains carbon monoxide in the range 20-35% vol, more preferably 25-35% vol.

The use of more reactive synthesis gas leads to smaller catalyst volumes being used, and the greater net heat of reaction gives a heat release per unit volume of catalyst which can be more than double that in a process based on steam reforming alone. Therefore providing effective cooling of the catalyst becomes more important as the carbon monoxide to carbon dioxide ratio in the synthesis gas increases.

The make-up gas may be combined with the first loop recycle gas stream to form the first synthesis gas mixture. The recycle loop stream contains hydrogen and therefore may enhance the methanol formation in the first synthesis reactor where the higher CO-content synthesis gases are used.

The composition of first synthesis gas at the first synthesis reactor inlet is preferably as follows; 15-30 mol % carbon monoxide, 0.5-10 mol % carbon dioxide, 55-85 mol % hydrogen and the balance one or more inert gases. The pressure of the first synthesis gas at the first synthesis reactor inlet is preferably 50-100 bar abs. The temperature of the first synthesis gas at the first synthesis reactor inlet is preferably 200-250° C. and at the outlet preferably 230-280° C.

The composition of second synthesis gas at the second synthesis reactor inlet is preferably as follows; 3-10 mol % carbon monoxide, 0.5-10 mol % carbon dioxide, 65-95 mol % hydrogen and the balance one or more inert gases. The pressure of the second synthesis gas at the second synthesis reactor inlet is preferably 50-100 bar abs. The temperature of the second synthesis gas at the second synthesis reactor inlet is preferably 215-250° C. and at the outlet preferably 250-300° C.

The loop recycle gas streams may be circulated by means of a two-stage circulator or alternatively by two separate circulators. By "two-stage circulator" we include a circulator that has two inlets and/or two outlets, for example as may be provided by a single casing containing two impellers with an offtake at an intermediate pressure between the first and second impellers and another offtake after the second impeller. Thus the loop recycle gas streams may be circulated by means of two circulators, which may be arranged either in a single casing having one inlet and two outlets at different pressures, a single casing having two inlets at different pressures and one outlet, or in two separate casings. Accordingly, in one embodiment, the circulator may comprise a first stage and a second stage where the first stage is fed with the first methanol-depleted gas mixture and the second stage is fed with the second recycle loop gas stream. The first methanol-depleted gas mixture and the second recycle loop gas stream are combined in the circulator which then provides the second synthesis gas, which may be heated and fed to the second synthesis reactor. The methanol-depleted gases fed to the circulator may be enriched if desired by a portion of the make-up gas. In an alternative embodiment, the first stage of a two-stage circulator may be fed with the second methanol-depleted gas stream (minus any purge gas) and produce two separate loop recycle gas streams; one, from the circulator first stage, which is fed to the second synthesis reactor and one from the circulator second stage, which is fed to the first synthesis reactor. In this case, the recycle loop gas fed to the second synthesis reactor may be diluted by the first methanol-depleted gas mixture, which may also contain a portion of the make-up gas. This arrangement provides the flexibility of switching the pressure of the first and second synthesis reactors. In an alternative embodiment, two circulators may be provided. A first circulator is fed with the first methanol-depleted gas mixture and a second circulator with the second methanol-depleted gas stream, minus any purge stream. The product of the second circulator is divided and portions fed to the first and second synthesis reactors. The portion fed to the second synthesis reactor is mixed with the first methanol-depleted gas stream coming from the first circulator. In this case, the product of the first circulator may if desired be diluted with a portion of the make-up gas. This arrangement provides the possibility of operating at the same pressure in the first and second synthesis reactors.

The present invention is able to minimise the recycle gas going back to the first synthesis reactor in order to minimise pressure drop and maximise reaction rate, while achieving the required dilution. In the process described in WO 2014012601 A1, the recycle stream back to first reactor has to be significantly larger because it is a mixture of unreacted gases from the first and second reactors, whereas by using the second methanol-depleted gas stream as the source of the recycle loop gas, the gas with the least carbon monoxide (CO) is used to dilute the first synthesis gas, which also has other advantages.

In the present invention, at least part of the second methanol-depleted gas mixture is used to form the first and second loop recycle gas streams. Thus, the second methanol-depleted gas may be divided into a first loop recycle gas stream, which is combined with make-up gas, and optionally other gas streams to form the first synthesis gas mixture, and a second loop recycle gas stream, which may optionally be combined with make-up gas and/or other gas streams to form the second synthesis gas mixture. A purge stream may be recovered from the second methanol-depleted gas and/or the first loop recycle gas stream and/or the second loop recycle gas stream.

If desired, for example, if shipping diameter is a limitation, in order to adjust the duty and so relative size of the first and second synthesis reactors, a proportion of the make-up gas may bypass the first synthesis reactor and enter the high recycle ratio loop as a secondary feed. Thus a portion of the make-up gas in the range 0-70% vol may be fed to the second synthesis reactor. However, for efficiency reasons, preferably the portion is ≤10% vol of the make-up gas and more preferably 0% vol, i.e. there is no by-pass, so that the process is operated in series.

The first synthesis reactor is preferably a design with a higher heat transfer relative to the cooled catalyst volume. The heat transfer can be conveniently characterised by the Volumetric UA. The Volumetric UA may be defined as the multiple of the overall heat transfer coefficient, U, times the total heat transfer area A, per cubic metre of cooled catalyst in the reactor. Although any converter could be used in this position, desirably the first synthesis reactor has a Volumetric UA of ≥50 kW/m$^3$/K and more preferably ≥90 kW/m$^3$/K. Such converters include those where the catalyst is disposed in a plurality of tubes that are cooled by a heat exchange medium.

The second synthesis reactor has a lower heat transfer relative to the cooled catalyst volume than the first synthesis reactor. For example, the Volumetric UA may be ≤40 kW/m$^3$/K. The second synthesis reactor can be of any type, but high overall conversion of carbon oxides into methanol is associated with high recycle flows or low converter exit temperature. There are several converter types that may be used and these include: (i) converters featuring one or more adiabatic beds and with no heat transfer surface in contact with the catalyst (ii) converters with gas cooling, such as a tube cooled converter, an isothermal methanol converter and a gas-cooled converter, and (iii) water-cooled converters with radial flow.

The first and second synthesis reactors may comprise one or more reactors.

In a preferred arrangement, the first synthesis reactor comprises a methanol synthesis catalyst disposed in tubes that are cooled by water under pressure, and the second synthesis reactor comprises a fixed bed of a methanol synthesis catalyst that is cooled in heat exchange with either water under pressure or a synthesis gas mixture selected from the first synthesis gas mixture and the second synthesis gas mixture.

Preferably the first synthesis reactor is an axial-flow, steam-raising converter (aSRC). In such reactors the synthesis gas typically passes axially through vertical, catalyst-containing tubes that are cooled in heat exchange with boiling water under pressure. The catalyst may be provided in pelleted form directly in the tubes or may be provided in one or more cylindrical containers that direct the flow of synthesis gas both radially and axially to enhance heat transfer. Such contained catalysts and their use in methanol synthesis are described in WO 02012146904 (A1). An aSRC typically has a Volumetric UA≥100 kW/m$^3$/K. Steam raising converters in which the catalyst is present in tubes cooled by boiling water under pressure offer a useful means to remove heat from the catalyst. However, while the aSRC offers the highest cooling factor, it makes poorer use of the reactor volume so the reactor shell is relatively large for the quantity of catalyst that it holds. Furthermore, aSRC's can suffer from a high pressure drop. By having a low recycle ratio to the first synthesis reactor the advantages of the aSRC are maximised while the disadvantages are minimised.

The second synthesis reactor may be a radial-flow steam raising converter, a gas-cooled converter or a tube cooled converter. In each of these, a bed of particulate catalyst is cooled by tubes or plates through which a coolant heat exchange medium passes. Alternatively the second synthesis reactor may be a quench reactor in which one or more beds of particulate catalyst are cooled by a synthesis gas mixture injected into the reactor within or between the beds.

In a radial-flow steam raising converter (rSRC) the synthesis gas typically passes radially (inwards or outwards) through a bed of particulate catalyst which is cooled by a plurality of tubes or plates through boiling water under pressure is fed as coolant. Such reactors are known and are described for example in U.S. Pat. No. 4,321,234. A rSRC has poorer heat transfer than an aSRC but has very low pressure drop, hence it favours operation with high recycle ratio. A rSRC typically has a Volumetric UA in the range 12-24 kw/m$^3$/K.

In a tube-cooled converter (TCC), the catalyst bed is cooled by feed synthesis gas passing through open-ended tubes disposed within the bed that discharge the heated gas to the catalyst. TCC's therefore can provide sufficient cooling area for a more reactive synthesis gas e.g. from combined reforming or coal gasification, but the increased heat of reaction would mean that the circulating loop gas flow would be insufficient to carry away the reaction heat unless the recycle ratio is high. A TCC typically has a Volumetric UA in the range 6-15 kW/m$^3$/K. As an alternative to a TCC, a gas cooled converter (GCC), may be used to cool the catalyst bed by passing the synthesis gas though tubes in a heat exchanger-type arrangement. A GCC is described for example in the aforesaid U.S. Pat. No. 5,827,901. The use of a TCC is preferred over the GCC in that it is simpler and cheaper to fabricate due to the use of open topped tubes and the elimination of the upper header and all of the differential expansion problems that the gas cooled converter raises. A TCC therefore has the advantage of low equipment cost and lower outlet temperature, which favours the synthesis reaction equilibrium, but it has a lower heat transfer than aSRC and higher pressure drop than rSRC.

In a quench reactor, the one or more beds of particulate catalyst are cooled by a synthesis gas mixture injected into the reactor within or between the beds. Accordingly, a quench reactor has a Volumetric UA of 0 kW/m$^3$/K. Such reactors are described, for example, in U.S. Pat. Nos. 3,458,289, 3,475,136 and 4,411,877.

Alternative converter designs, such as the Linde Variobar converter comprising a bed of methanol synthesis catalyst cooled in heat exchange with boiling water passing through a spiral-wound heat exchanger within the bed, typically have an intermediate Volumetric UA of 30-40 kW/m$^3$/K. Such converters may be used as the second synthesis reactor in combination, for example, with an axial-flow steam-raising converter, or may be used as the first synthesis reactor in combination with a quench reactor, a tube-cooled converter or even a radial-flow steam-raising converter.

The methanol synthesis catalysts are preferably copper-containing methanol synthesis catalysts, in particular the methanol synthesis catalyst in the first and second synthesis reactors is a particulate copper/zinc oxide/alumina catalyst. Particularly suitable catalysts are Mg-doped copper/zinc oxide/alumina catalysts as described in U.S. Pat. No. 4,788,175. The same or different methanol synthesis catalysts may be used in the first and second synthesis reactors.

Methanol synthesis may be effected in the first and second synthesis reactors at elevated temperature and pressure, for example pressures in the range 20 to 120 bar abs and temperatures in the range 130° C. to 350° C. Where two-stage or separate circulation is effected for the recycle loop gas streams to the first and second synthesis reactors, they may be operated at the same or different pressures. Thus the first reactor may be operated at a higher pressure, the same pressure or a lower pressure than the second reactor. This may provide advantages in methanol recovery. In a preferred embodiment, the pressure in the second synthesis reactor is higher than the pressure in the first synthesis reactor. The difference in pressure between the reactors may be ≥4 bar. The circulators may be conventional compressors suitably adapted for processing the recycle loop gas at the desired pressures.

The product gas stream withdrawn from the second synthesis reactor typically has a temperature in the range from 180 to 250° C., preferably 200-300° C.

The proportion of the methanol made in the first and second reactors may be in the range 30:70 to 70:30, for example 40:60 to 60:40 or 50:50.

The gas mixtures fed to the first and second synthesis reactors may be heated before being fed to the reactors. The heating may be effected by conventional heat exchange using a suitable heat exchange apparatus. If a gas-cooled converter (GCC) is used, at least part of the first or second synthesis gas mixture may be heated by passing it through heat exchange tubes or plates disposed within a catalyst bed disposed in the second synthesis reactor. Preferably, the first and/or second synthesis gases are heated in gas-gas heat exchangers using the product gases from the reactors. Other temperature adjustment of the feed or product gases may be performed using conventional heat exchange apparatus. Thus the product gas streams from the first and second synthesis reactors may be cooled in one or more stages of heat exchange, e.g. with water or air cooling, to condense methanol therefrom, which may suitably be recovered using gas-liquid separators. The cooling may be performed to fully or partially condense the methanol from the first and second product gas streams. Preferably essentially all of the methanol is condensed from the second product gas stream. The recovered liquid methanol streams may be processed separately but are preferably combined and passed for further processing, such as one or more, preferably two or three, stages of distillation to produce a purified methanol product.

A purge gas stream is preferably recovered from the loop to avoid the build-up of inert gases, such as nitrogen, methane and argon. The purge gas typically comprises hydrogen and carbon oxides and may be used for hydrogen recovery, for example by pressure-swing absorption or by using suitable membranes, or may be subjected to one or more further processing stages including autothermal reforming, water-gas shift and methanol synthesis.

The purge may be recovered from the first methanol-depleted gas or the second methanol depleted gas depending on whether the stoichiometry of the make-up gas is hydrogen-rich or carbon-rich. Preferably the purge is recovered from the second methanol depleted gas mixture and the remaining methanol depleted gas mixture used as the recycle loop gas mixture.

The invention will be further described by reference to the figures in which.

It will be understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

Figure 1:
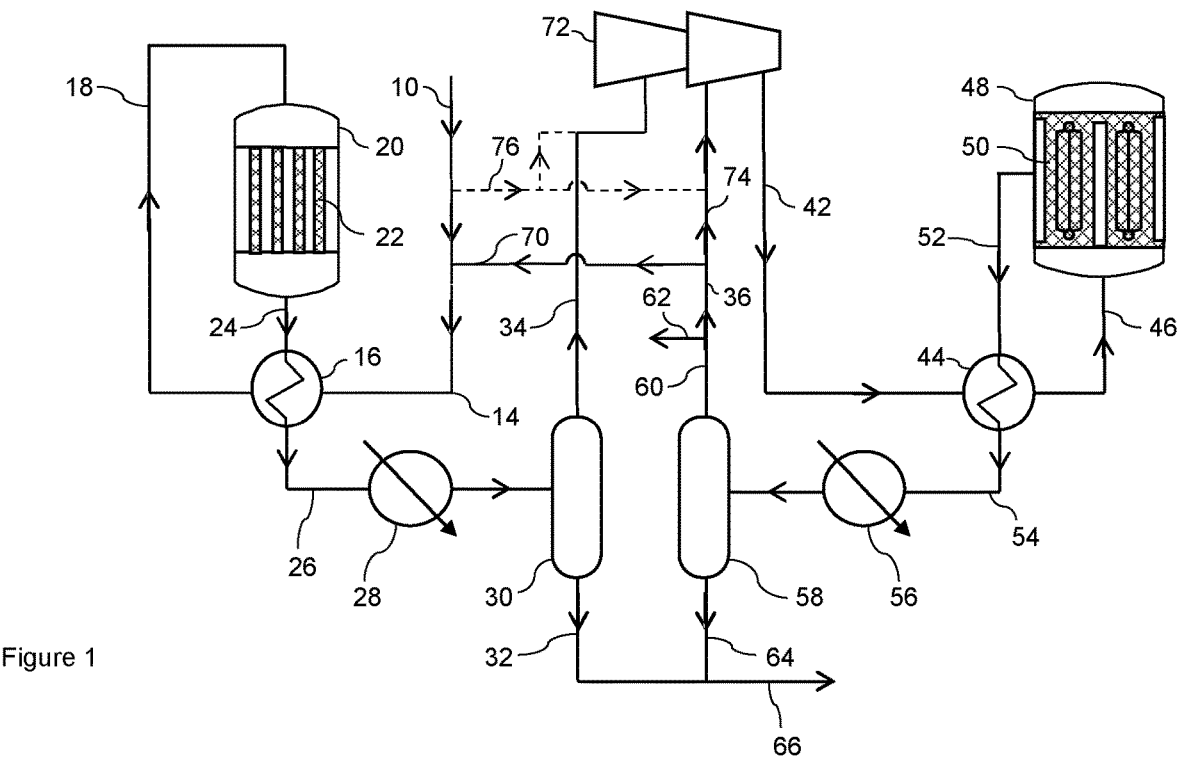
FIG. 1 depicts a process according to an embodiment of the present invention utilising an aSRC and rSRC where the second reactor is at a higher pressure than the first reactor.

In FIG. 1, a make-up gas in line 10 comprising hydrogen, carbon monoxide and carbon dioxide is combined with a first recycle loop gas stream 70 and the resulting first synthesis gas mixture passed via line 14 to a gas-gas interchanger 16 where it is heated in indirect heat exchange with a first product gas stream 24. The heated first synthesis gas mixture is fed by line 18 to the inlet of an axial steam-raising converter 20, containing catalyst-filled tubes 22 through which the synthesis gas mixture is passed. The tubes are cooled by boiling water under pressure. The catalyst is a particulate copper/zinc oxide/alumina catalyst. The boiling water under pressure is fed to the shell side of the reactor and a mixture of boiling water and steam is withdrawn and supplied to a steam drum (not shown). The methanol synthesis reaction takes place as the synthesis gas passes axially through the catalyst-filled tubes 22 to form a first product gas stream containing methanol vapour. The first product gas stream is recovered from the outlet of the first synthesis reactor 20 and fed via line 24 to the interchanger 16 where it is partially cooled. The partially cooled gas is fed via line 26 to one or more further stages of heat exchange 28 to condense methanol therefrom. The resulting gas-liquid mixture is passed to a gas-liquid separator 30 and liquid methanol is recovered via line 32. A first methanol-depleted gas mixture comprising unreacted hydrogen and carbon oxides is recovered from the separator 30 and fed by line 34 to the first stage of a two-stage circulator 72. The second stage of the two-stage circulator 72 is fed with a second recycle loop gas fed by line 74. The first methanol-depleted gas 34 and the second recycle loop gas 74 are combined in the circulator 72 to form a second synthesis gas mixture. The circulator compresses the second synthesis gas mixture which is fed from the circulator by line 42 to a gas-gas interchanger 44 where it is heated in indirect heat exchange with a second product gas stream 52. The heated second synthesis gas is fed by line 46 to the inlet of a radial steam-raising converter 48 containing a bed of methanol synthesis catalyst 50, containing a plurality of heat exchange tubes though which boiling water under pressure is passed as coolant. Whereas tubes are depicted, alternative heat exchange devices such as plates through which the coolant may be passed, may also be used. The catalyst is a particulate copper/zinc oxide/alumina catalyst. The boiling water under pressure is fed to the tube side of the reactor and a mixture of boiling water and steam is withdrawn and supplied to a steam drum (not shown). The methanol synthesis reaction takes place as the synthesis gas passes radially through the bed of catalyst 50 to form a second product gas stream containing methanol vapour. The second product gas stream is recovered from the outlet of the second synthesis reactor 48 and fed via line 52 to the interchanger 44 where it is partially cooled. The partially cooled gas is fed via line 54 to one or more further stages of heat exchange 56 to condense methanol therefrom. The resulting gas liquid mixture is passed to a gas-liquid separator 58 and liquid methanol is recovered via line 64. A second methanol-depleted gas mixture is recovered in the separator 58 and fed by line 60 to a purge off-take line 62, which removes a portion of the gas to reduce the build-up of inert gases. The remaining second methanol-depleted gas mixture in line 36 is divided to form the first recycle loop gas 70 and the second recycle loop gas 74. The crude methanol streams 32 and 64 are combined and send by line 66 for further processing such as one or more stages of distillation to produce a purified methanol product.

A portion of the make-up gas may be diverted from line 10 by dotted-line 76 to line 34 and/or line 74 fed to the circulator 72. This may be done in order to adjust the duty and so the relative sizes of the first and second synthesis reactors, or may also be used to enrich the second synthesis gas. Where the portion of make-up gas 76 is fed to line 74, a suitable control valve on line 10 may be used to control the flow.

Figure 2:
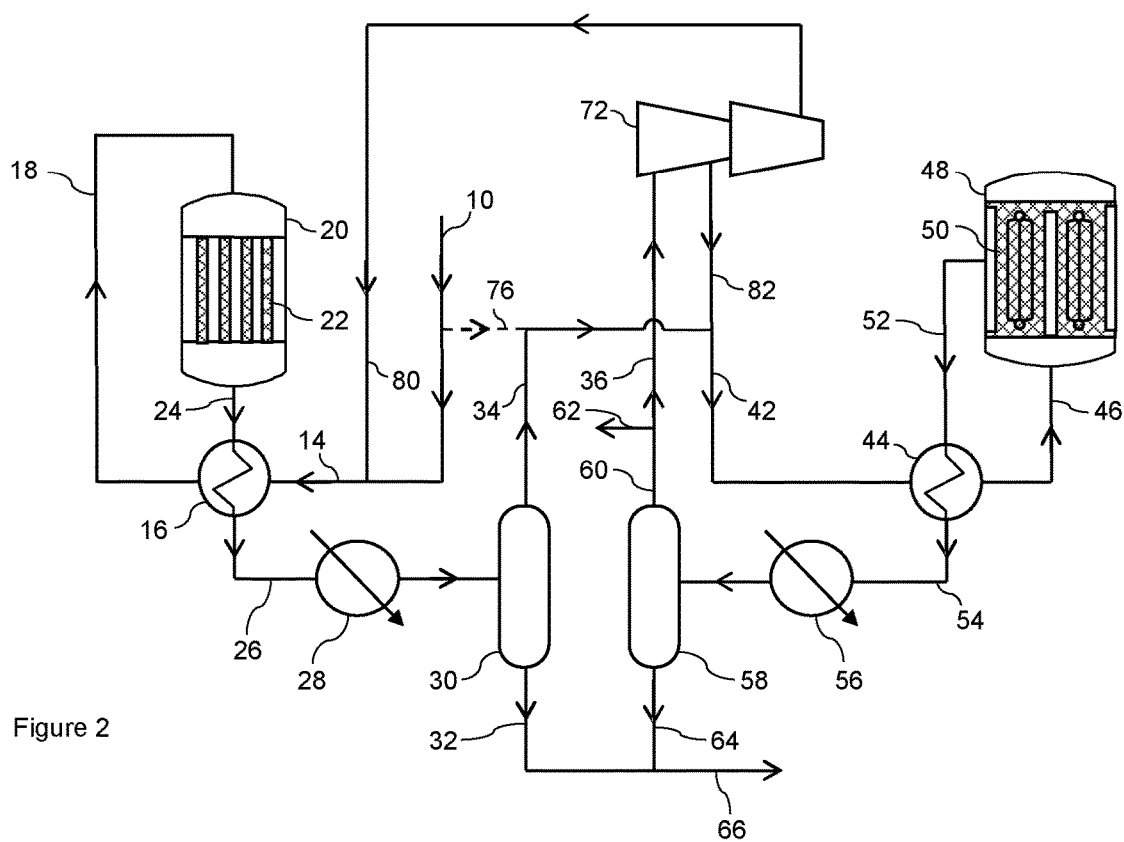
FIG. 2 depicts a process according to an embodiment of the present invention utilising an aSRC and rSRC where the second reactor is at a lower pressure than the first reactor.

In FIG. 2, the two-stage circulator is configured to produce separate recycle loop gas streams. Such an arrangement provides the flexibility of switching the pressure of first and second synthesis reactors. Thus in FIG. 2 a make-up gas fed via line 10 is mixed with a first recycle loop gas containing hydrogen, fed by line 80, to form the first synthesis gas mixture 14. The first synthesis gas mixture is converted in the first synthesis reactor 20 in the same manner as depicted in FIG. 1. The first methanol depleted gas mixture 34 is mixed with a second recycle loop gas 82 to form the second synthesis gas mixture 42. The second synthesis gas mixture is converted in the second synthesis reactor in the same manner as depicted in FIG. 1. The second methanol-depleted gas recovered from the gas-liquid separator 58 is fed by line 60 to a purge off-take line 62, which removes a portion of the gas to reduce the build-up of inert gases. The remaining second methanol-depleted gas mixture is fed to the first stage of the circulator 72 by line 36. The first stage of the circulator provides the second recycle loop gas 82 used to form the second synthesis gas mixture 42. The second stage of the circulator 72 provides the first recycle loop gas stream 80. The crude methanol streams 32 and 64 are again combined and send by line 66 for further processing such as one or more stages of distillation to produce a purified methanol product.

A portion of the make-up gas may be diverted from line 10 by dotted-line 76 to line 34 used to prepare the second synthesis gas mixture 42. This may be done in order to adjust the duty and so the relative sizes of the first and second synthesis reactors, and/or may also be used to enrich the second synthesis gas to enhance overall process efficiency.

Figure 3:
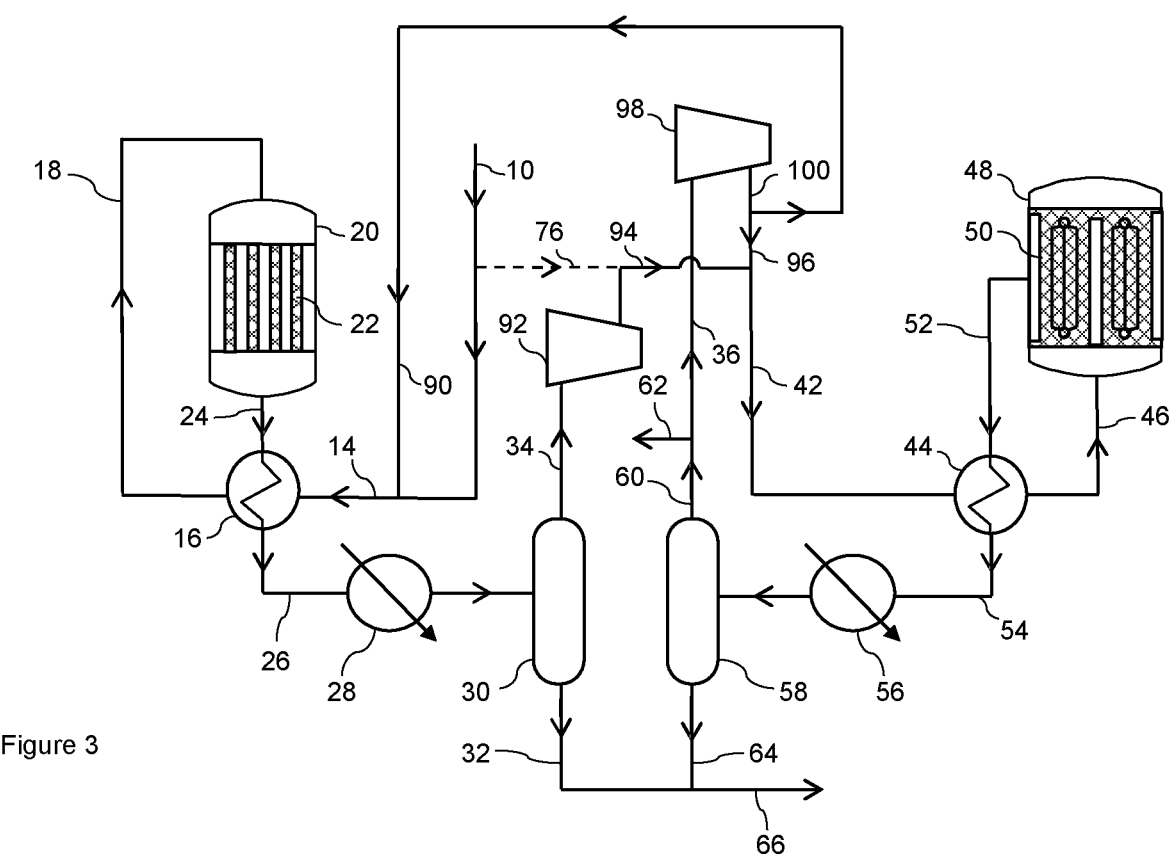
FIG. 3 depicts a process according to an embodiment of the present invention utilising an aSRC and rSRC where both reactors are at a similar pressure.

In FIG. 3, two separate circulators are used to produce separate recycle loop gas streams. Such an arrangement provides the ability to operate the first and second synthesis reactors at the same pressure. Thus in FIG. 3 a make-up gas fed via line 10 is mixed with a first recycle loop gas containing hydrogen, fed by line 90, to form the first synthesis gas mixture 14. The first synthesis gas mixture is converted in the first synthesis reactor 20 in the same manner as depicted in FIG. 1. The first methanol-depleted gas mixture is passed by line 34 to a first circulator 92 where it is compressed and passed by line 94 to be mixed with a second recycle loop gas in line 96 to form the second synthesis gas mixture 42. The second synthesis gas mixture is converted in the second synthesis reactor in the same manner as depicted in FIG. 1. The second methanol-depleted gas recovered from the gas-liquid separator 58 is fed by line 60 to a purge off-take line 62, which removes a portion of the gas to reduce the build-up of inert gases. The remaining second methanol-depleted gas mixture is fed by line 36 to a second circulator 98. The second circulator provides a compressed recycle loop gas stream 100 which is divided to provide the first recycle loop gas 90 use to prepare the first synthesis gas mixture 14, and the second recycle loop gas 96 use to prepare the second synthesis gas mixture 42. The crude methanol streams 32 and 64 are again combined and send by line 66 for further processing such as one or more stages of distillation to produce a purified methanol product.

A portion of the make-up gas may be diverted from line 10 by dotted-line 76 to line 94 used to prepare the second synthesis gas mixture 42. This may be done in order to adjust the duty and so the relative sizes of the first and second synthesis reactors, and/or may also be used to enrich the second synthesis gas to enhance overall process efficiency.

The same processes as depicted in FIGS. 1-3 may be performed replacing the radial steam raising converter 48 with a tube-cooled converter in which the catalyst bed is cooled in direct heat exchange with the second synthesis gas. Thus in each case, the second synthesis gas may be fed from heat exchanger 44 via line 46 to the bottom of a tube cooled converter and passed upwards through a plurality of tubes disposed within the catalyst bed. The gas is heated as it passes upwards through tubes. The heated gas exits the tubes within the reactor above the bed and then passes down through the bed where it reacts to form a gas mixture containing methanol vapour. The product gas may be collected and fed via line 52 to heat exchanger 44 where it is cooled.

The Invention is further illustrated by reference to the following Example.

EXAMPLE 1

A computer model of a process according to the present invention was developed and compared against a process where there is a single common circulator operating at either a high or low recycle ratio. The benefits of operating the process in which the recycle ratios are different for the different reactors are as follow:
1. When compared to the process operating at a high recycle ratio, the present invention achieves the same catalyst and feed efficiency and benefits from higher energy efficiency and smaller piping and loop equipment.
2. When compared to the process operating at a low recycle ratio, the present invention achieves higher catalyst and feed efficiency. It also benefits from operating at lower pressure to achieve the same feed efficiency.

If the process of U.S. Pat. No. 7,790,775, operating with two radial-flow steam-raising converters at a molar recycle ratio of 3.38, is compared with the process of FIG. 1 operating with a molar recycle ratio of 0.55 for the axial-flow steam raising converter and 2.50 for the radial-flow steam-raising converter, the following figures are obtained;

| Configuration | Comparative Example | FIG. 1 |
|---|---|---|
| Capacity, MTPD | 5500 | 5500 |
| Methanol production | 50% rSRC and 50% rSRC | 60% aSRC and 40% rSRC |
| Total catalyst, m$^3$ | 182.8 | 159.6 |
| Reactor pressure, bara | 76.0/80.0 | 76.0/80.0 |
| Total Converter heat removed as steam, MW | 148.05 | 167.53 |
| Circulator Power, MW | 10.05 | 5.61 (2 stage total) |
| Syngas Comp Power, MW | 9.21 | 9.21 |
| Total Compressor Power, MW | 19.26 | 14.82 |

The benefit of the present invention is that a lower catalyst volume is required, higher steam production is achieved and lower compression power is required. Accordingly, the present invention is also able to provide significant equipment cost and energy savings.

The compositions, temperatures and pressures of for the streams depicted in FIG. 1 are set out in the following tables.

| | Stream | | | | | | | |
|---|---|---|---|---|---|---|---|---|
| | 10 | 14 | 18 | 24 | 32 | 34 | 42 | 46 |
| Pressure MPa(abs) | 7.7 | 7.7 | 7.6 | 7.4 | 7.1 | 7.1 | 8.2 | 8.1 |
| Temperature ° C. | 120 | 93 | 225 | 255 | 45 | 45 | 55 | 240 |
| Flow kNm$^3$/hr (vapour) | 520 | 811 | 811 | 613 | | 512 | 1521 | 1521 |
| Flow Tonne/hr (liquid) | | | | | 142.8 | | | |
| Composition Mole % | | | | | | | | |
| H$_2$O | 0.5 | 0.3 | 0.3 | 0.3 | 1.8 | 0.0 | 0.0 | 0.0 |
| H$_2$ | 67.6 | 73.4 | 73.4 | 65.0 | 0.4 | 77.7 | 81.8 | 81.8 |
| CO | 29.4 | 19.7 | 19.7 | 9.7 | 0.3 | 11.6 | 5.5 | 5.5 |
| CO$_2$ | 1.9 | 1.6 | 1.6 | 2.3 | 0.8 | 2.6 | 1.5 | 1.5 |
| CH$_3$OH | 0.0 | 0.2 | 0.2 | 16.4 | 96.4 | 0.7 | 0.6 | 0.6 |
| Inerts | 0.7 | 4.8 | 4.8 | 6.3 | 0.2 | 7.5 | 10.5 | 10.5 |

| | Stream | | | | | |
|---|---|---|---|---|---|---|
| | 52 | 60 | 62 | 64 | 70 | 74 | 76 |
| Pressure MPa(abs) | 8.0 | 7.7 | 7.7 | 7.7 | 7.7 | 7.7 | 7.7 |
| Temperature ° C. | 270 | 45 | 45 | 45 | 45 | 45 | 120 |
| Flow kNm$^3$/hr (vapour) | 1399 | 1326 | 26 | | 291 | 1009 | 0 |

-continued

| | Stream | | | | | | |
|---|---|---|---|---|---|---|---|
| | 52 | 60 | 62 | 64 | 70 | 74 | 76 |
| Flow Tonne/hr (liquid) | | | | 98.0 | | | |
| Composition Mole % | | | | | | | |
| $H_2O$ | 0.7 | 0.0 | 0.0 | 13.1 | 0.0 | 0.0 | 0.5 |
| $H_2$ | 79.5 | 83.9 | 83.9 | 0.4 | 83.9 | 83.9 | 67.6 |
| CO | 2.3 | 2.5 | 2.5 | 0.1 | 2.5 | 2.5 | 29.4 |
| $CO_2$ | 1.0 | 1.0 | 1.0 | 0.3 | 1.0 | 1.0 | 1.9 |
| $CH_3OH$ | 5.0 | 0.6 | 0.6 | 85.9 | 0.6 | 0.6 | 0.0 |
| Inerts | 11.4 | 12.0 | 12.0 | 0.3 | 12.0 | 12.0 | 0.7 |

The invention claimed is:

1. A process for synthesizing methanol comprising the steps of:
   (i) passing a first synthesis gas mixture comprising a make-up gas and a first loop recycle gas stream through a first synthesis reactor containing a first cooled methanol synthesis catalyst to form a first product gas stream,
   (ii) recovering methanol from the first product gas stream to form a first methanol-depleted gas mixture,
   (iii) combining the first methanol-depleted gas mixture with a second loop recycle gas stream to form a second synthesis gas mixture,
   (iv) passing the second synthesis gas mixture through a second synthesis reactor containing a second cooled methanol synthesis catalyst to form a second product gas stream,
   (v) recovering methanol from the second product gas stream to form a second methanol-depleted gas mixture, and
   (vi) forming the first and second loop recycle gas streams from the second methanol-depleted gas mixture,
   wherein the first synthesis reactor has a higher heat transfer per cubic metre of catalyst than the second synthesis reactor and the recycle ratio of the first loop recycle gas stream to form the first synthesis gas mixture is in the range of from 0.1 to 1:1, and the recycle ratio of the second loop recycle gas stream to form the second synthesis gas mixture is in the range of from 1.1:1 to 6:1.

2. The process according to claim 1 wherein the recycle ratio of the loop recycle gas stream to form the second synthesis gas mixture is in the range of from 1.5:1 to 6:1.

3. The process according to claim 1 wherein the make-up gas contains carbon monoxide in the range of from 20 to 35% vol.

4. The process according to claim 1 wherein the loop recycle gas streams are circulated by means of a two-stage circulator comprising a first stage and a second stage, or two separate circulators.

5. The process according to claim 4 wherein a circulator comprises a first stage and a second stage, the first stage is fed with the first methanol-depleted gas mixture and the second stage is fed with the second recycle loop gas stream, and the first methanol-depleted gas mixture and the second recycle loop gas stream are combined in the circulator to provide the second synthesis gas.

6. The process according to claim 5 wherein the methanol-depleted gases fed to the circulator are enriched by a portion of the make-up gas.

7. The process according to claim 4 wherein a circulator comprises a first stage and a second stage, the first stage is fed with the second methanol-depleted gas stream minus any purge gas and produces two separate loop recycle gas streams; one from the circulator first stage, which is combined with the first methanol-depleted gas mixture and fed to the second synthesis reactor, and one from the circulator second stage, which is fed to the first synthesis reactor.

8. The process according to claim 7 wherein the first methanol-depleted gas mixture contains a portion of the make-up gas.

9. The process according to claim 4 wherein two separate circulators are used, a first circulator is fed with the first methanol-depleted gas mixture and a second circulator is fed with the second methanol-depleted gas stream, minus any purge stream, the second circulator product is divided into the first and second recycle loop gas streams, and the second recycle loop gas stream is mixed with the first methanol-depleted gas stream product of the first circulator.

10. The process according to claim 9 where the first methanol-depleted gas stream product of the first circulator is diluted with a portion of the make-up gas.

11. The process according to claim 1 wherein the first synthesis reactor comprises the first methanol synthesis catalyst disposed in tubes that are cooled by water under pressure, and the second synthesis reactor comprises a fixed bed of the second methanol synthesis catalyst that is cooled in heat exchange with either water under pressure or a synthesis gas mixture that is the first synthesis gas mixture or the second synthesis gas mixture.

12. The process according to claim 1 wherein the first synthesis reactor is an axial flow steam-raising converter.

13. The process according to claim 1 wherein the second synthesis reactor is a radial flow steam-raising converter, a tube-cooled converter, a gas-cooled converter or a quench reactor.

14. The process according to claim 1 wherein the first, second, or first and second cooled methanol synthesis catalysts are copper-containing methanol synthesis catalysts.

15. The process according to claim 1 wherein methanol synthesis in the first and second reactors is performed at pressures in the range of from 20 to 120 bar abs and temperatures in the range of from 130° C. to 350° C.

16. The process according to claim 15 wherein the pressure in the second synthesis reactor is higher than the pressure in the first synthesis reactor.

17. The process according to claim 1 wherein the gas mixtures fed to the first and/or second synthesis reactors are heated in gas-gas heat exchangers using the product gases from the reactors.

18. The process according to claim 1 wherein the product gas streams from the first and second synthesis reactors are cooled in one or more stages of heat exchange to condense methanol therefrom.

19. The process according to claim 1 wherein a purge gas stream is recovered from the second methanol depleted gas mixture and is used for hydrogen recovery, or is subjected to one or more further processing stages including autothermal reforming, water-gas shift, or methanol synthesis.

20. The process according to claim 1 wherein the recycle ratio of the loop recycle gas stream to form the second synthesis gas mixture is in the range of from 2:1 to 6:1.

21. The process according to claim 1 wherein the loop recycle gas streams are circulated by means of two circulators arranged either in a single casing having one inlet and two outlets at different pressures, a single casing having two inlets at different pressures and one outlet, or in two separate casings.

22. The process according to claim 1 wherein the first, second, or first and second cooled methanol synthesis catalysts are compositions comprising copper, zinc oxide and alumina.

23. The process according to claim 18, wherein the condensed methanol is recovered and subjected to further processing by one or more stages of distillation to produce a purified methanol product.

* * * * *